United States Patent
Takahashi et al.

(10) Patent No.: US 12,094,037 B2
(45) Date of Patent: Sep. 17, 2024

(54) MEDICAL IMAGE PROCESSING APPARATUS AND MEDICAL IMAGE PROCESSING METHOD

(71) Applicant: FUJIFILM Healthcare Corporation, Kashiwa (JP)

(72) Inventors: Hisashi Takahashi, Kashiwa (JP); Taiga Goto, Kashiwa (JP); Kana Tanaka, Kashiwa (JP)

(73) Assignee: FUJIFILM Healthcare Corporation, Chiba (JP)

( * ) Notice: Subject to any disclaimer, the term of this patent is extended or adjusted under 35 U.S.C. 154(b) by 386 days.

(21) Appl. No.: 17/645,473

(22) Filed: Dec. 22, 2021

(65) Prior Publication Data
US 2022/0245871 A1    Aug. 4, 2022

(30) Foreign Application Priority Data

Feb. 2, 2021    (JP) .................................. 2021-015118

(51) Int. Cl.
*G06V 10/00* (2022.01)
*A61B 6/00* (2006.01)
(Continued)

(52) U.S. Cl.
CPC ............ *G06T 11/008* (2013.01); *A61B 6/032* (2013.01); *A61B 6/5235* (2013.01);
(Continued)

(58) Field of Classification Search
CPC ...... G06V 10/25; G06V 2201/03; G06T 7/10; G06T 7/0012; G06T 5/70; G06T 11/008;
(Continued)

(56) References Cited

U.S. PATENT DOCUMENTS

| | | | | |
|---|---|---|---|---|
| 5,440,647 A * | 8/1995 | Floyd, Jr. | .................. | G06T 5/70 382/254 |
| 8,175,360 B2 * | 5/2012 | Razifar | ................. | G06T 11/005 382/131 |
| 8,233,689 B2 * | 7/2012 | Razifar | ................. | G06T 7/0012 382/131 |
| 8,761,540 B2 * | 6/2014 | Yang | .................... | G06T 11/008 382/275 |

(Continued)

FOREIGN PATENT DOCUMENTS

| | | |
|---|---|---|
| JP | 2018-000618 A | 1/2018 |
| JP | 6713860 | 6/2020 |

OTHER PUBLICATIONS

Ohashi et al., "JP H0951891A1 Computer tomography"; date published Feb. 25, 1997.*

(Continued)

*Primary Examiner* — Amir Alavi
(74) *Attorney, Agent, or Firm* — Paul Teng (57) ABSTRACT

There are a medical image processing apparatus and a medical image processing method that are capable of maintaining the estimation accuracy of noise intensity even though a system noise ratio rises. A medical image processing apparatus includes a difference image generating unit that divides projection data obtained by applying radiation to an examinee to create a difference image between tomographic images reconstructed for every divided piece of projection data; a local variance computing unit that computes local variance in the difference image; and a noise estimation unit that corrects the local variance using a correction function found in advance to estimate noise intensity of a tomographic image of the examinee. The correction function includes system noise.

17 Claims, 9 Drawing Sheets

(51) Int. Cl.
  *A61B 6/03* (2006.01)
  *G06T 5/70* (2024.01)
  *G06T 7/00* (2017.01)
  *G06T 11/00* (2006.01)
  *G06V 10/25* (2022.01)
  *G16H 30/40* (2018.01)

(52) U.S. Cl.
  CPC .............. *A61B 6/5258* (2013.01); *G06T 5/70* (2024.01); *G06T 7/0012* (2013.01); *G06V 10/25* (2022.01); *G16H 30/40* (2018.01); *G06T 2207/10072* (2013.01); *G06T 2207/30004* (2013.01); *G06V 2201/03* (2022.01)

(58) Field of Classification Search
  CPC . G06T 2207/10081; G06T 2207/10116; G06T 2207/30004; A61B 6/5211; A61B 6/032; A61B 6/035; A61B 6/5235; A61B 6/5258; A61B 6/563; G16H 30/40
  See application file for complete search history.

(56) References Cited

U.S. PATENT DOCUMENTS

| | | | |
|---|---|---|---|
| 8,942,445 B2* | 1/2015 | Foo | G06T 7/11 |
| | | | 382/128 |
| 8,965,095 B2* | 2/2015 | Zou | A61B 6/5258 |
| | | | 378/4 |
| 10,028,712 B2* | 7/2018 | Allinson | G01T 1/2985 |
| 10,878,602 B2* | 12/2020 | Takahashi | G06T 11/005 |
| 11,234,666 B2* | 2/2022 | Chan | G06T 7/0012 |
| 11,328,391 B2* | 5/2022 | Li | G06F 18/22 |
| 11,918,390 B2* | 3/2024 | Heukensfeldt Jansen | |
| | | | A61B 6/037 |
| 2019/0180482 A1 | 6/2019 | Takahashi et al. | |
| 2019/0385345 A1* | 12/2019 | Bergner | G06T 11/006 |

OTHER PUBLICATIONS

Japanese official action dated Aug. 22, 2023 (and machine translation) in connection with Japanese Patent Application No. 2021-015118.

* cited by examiner

MEDICAL IMAGE PROCESSING APPARATUS AND MEDICAL IMAGE PROCESSING METHOD

CROSS-REFERENCE TO RELATED APPLICATION

The present application claims priority from Japanese Patent Application JP 2021-015118 filed on Feb. 2, 2021, the content of which is hereby incorporated by reference into this application.

TECHNICAL FIELD

The present invention relates to a medical image processing apparatus and a medical image processing method that handle medical images obtained with an X-ray computed tomography (CT) apparatus, and relates to a technique that estimates the noise intensity of a medical image.

BACKGROUND OF THE INVENTION

An X-ray computed tomography apparatus is an apparatus that applies X-rays from the surrounding areas of an examinee to acquire projection data at a plurality of projection angles and the projection data is back-projected to reconstruct tomographic images for image diagnosis. In the X-ray computed tomography apparatus, in order to reduce the exposure of the examinee to X rays, the improvement of the image quality of tomographic images is intended based on local noise intensity estimated on the tomographic images obtained by low dose imaging.

Japanese Patent No. 6713860 discloses that a tomographic image is reconstructed for each divided piece of projection data, fluctuations in pixel values computed on a between tomographic images are corrected using correction values found in advance, and thus noise intensity is estimated.

However, in Japanese Patent No. 6713860 gives no consideration on system noise that increases with a cost reduction in an X-ray detector, and the estimation accuracy of noise intensity is reduced as a system noise ratio rises.

SUMMARY OF THE INVENTION

Therefore, an object of the present invention is to provide a medical image processing apparatus and a medical image processing method that are capable of maintaining the estimation accuracy of noise intensity even though a system noise ratio rises.

In order to achieve the object, an aspect of the present invention is a medical image processing apparatus including: a difference image generating unit that divides projection data obtained by applying radiation to an examinee to create a difference image between tomographic images reconstructed for every divided piece of projection data; a local variance computing unit that computes local variance in the difference image; and a noise estimation unit that corrects the local variance using a correction function found in advance to estimate noise intensity of a tomographic image of the examinee. The correction function includes system noise.

Furthermore, another aspect of the present invention is a difference image creating step in which projection data obtained by applying radiation to an examinee is divided to create a difference image between tomographic images reconstructed for every divided piece of projection data; a local variance computing step in which local variance is computed in the difference image; and a noise estimating step in which the local variance is corrected using a correction function found in advance to estimate noise intensity of a tomographic image of the examinee. The correction function includes system noise.

According to the present invention, it is possible to provide a medical image processing apparatus and a medical image processing method that are capable of maintaining the estimation accuracy of noise intensity even though a system noise ratio rises.

DETAILED DESCRIPTION OF THE PREFERRED EMBODIMENTS

In the following, embodiments of a medical image processing apparatus and a medical image processing method according to the present invention will be described. Note that in the following description and the accompanying drawings, components having the same functional configurations are designated with the same reference signs, and redundant description is omitted.

First Embodiment

Figure 1:
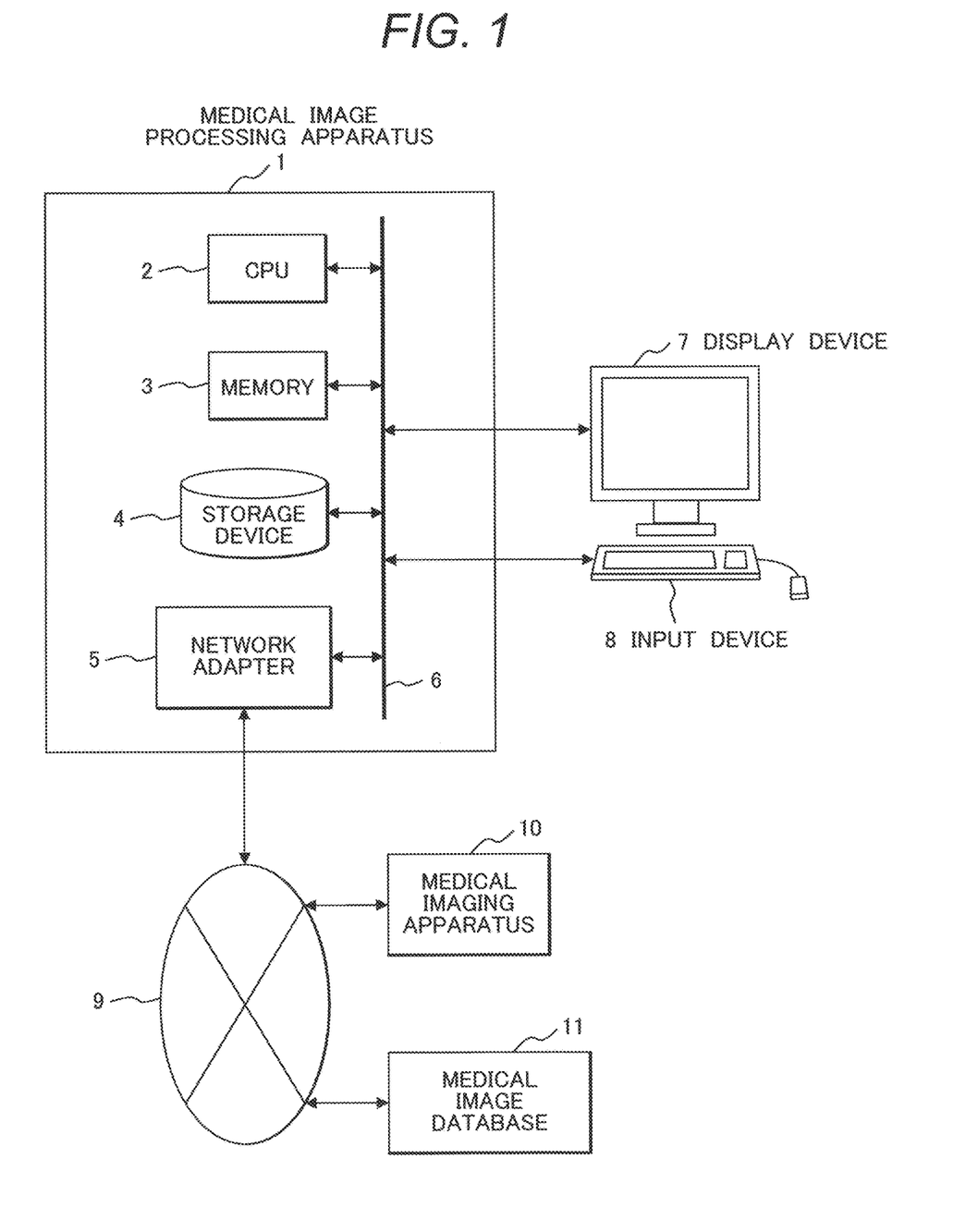
FIG. 1 is a diagram of the overall structure of a medical image processing apparatus.

FIG. 1 is a diagram showing the hardware configuration of a medical image processing apparatus 1. The medical image processing apparatus 1 includes a central processing unit (CPU) 2, a memory 3, a storage device 4, and a network adapter 5, which are connected to each other, as these components are capable of transmitting and receiving signals through a system bus 6. The medical image processing apparatus 1 is connected to a medical imaging apparatus 10 and a medical image database 11 so as to be capable of transmitting and receiving signals via a network 9, and a display device 7 and an input device 8 are connected. Here, the phrase "capable of transmitting and receiving signals" means a state where signals can be transmitted and received mutually or one side to the other side, regardless of an electrical manner or optical manner.

The CPU 2 is a device that controls the operations the components. The CPU 2 loads a program stored in the storage device 4 or loads data necessary to execute a program to the memory 3 for execution, and applies various image processes to medical images. The memory 3 is a component that stores the program executed by the CPU 2 or that stores events in progress of arithmetic operation processes. The storage device 4 is a device that stores the program executed by the CPU 2 and data necessary to execute the program. Specifically, the storage device 4 is a Hard Disk Drive (HHD) and Solid State Drive, for example. The network adapter 5 is a device that connects the medical image processing apparatus 1 to the network 9 such as a local area network (LAN), a telephone line, and Internet. Various items of data handled by the CPU 2 may be transmitted to and received from the outside of the medical image processing apparatus 1 via the network 9 such as a LAN.

The display device 7 is a device that displays processed results and the like of the medical image processing apparatus 1, and specifically, the display device 7 is a liquid crystal display, for example. The input device 8 is an operation device through which an operator instructs the medical image processing apparatus 1 to conduct operation, and specifically, the input device 8 is a keyboard, a mouse, a touch panel, and the like. The mouse may be a pointing device such as a track pad and a track ball.

The medical imaging apparatus 10 is an X-ray CT apparatus that acquires, for example, the projection data of an examinee to reconstruct tomographic images from the projection data, and the medical imaging apparatus 10 will be described later with reference to FIG. 2. The medical image database 11 is a database system that stores projection data, tomographic images, and the like acquired by the medical imaging apparatus 10.

Figure 2:
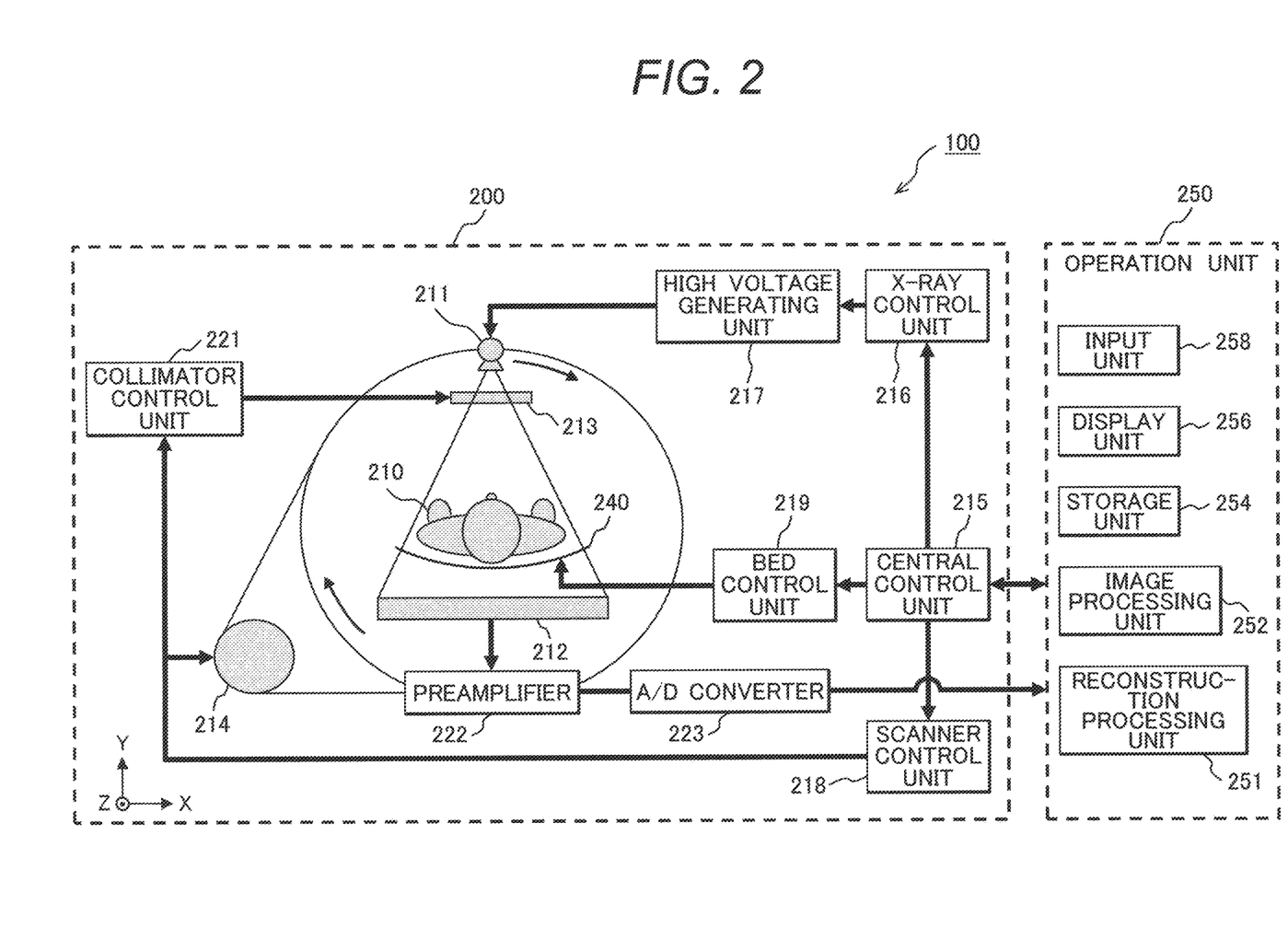
FIG. 2 is a diagram of the overall structure of an X-ray computed tomography apparatus that is an example of the medical imaging apparatus.

Referring to FIG. 2, the overall structure of an X-ray computed tomography apparatus 100 that is an example of the medical imaging apparatus 10 will be described. Note that in FIG. 2, the lateral direction is set as an X-axis, the vertical direction is set as a Y-axis, and a direction vertical to the paper surface is set as a Z-axis. The X-ray computed tomography apparatus 100 includes a scanner and an operation unit 250.

The scanner 200 has an X-ray tube 211, a detector 212, a collimator 213, a drive unit 214, a central control unit 215, an X-ray control unit 216, a high voltage generating unit 217, a scanner control unit 218, a bed control unit 219, a collimator control unit 221, a preamplifier 222, an A/D converter 223, a bed 240, and the like.

The X-ray tube 211 is a device that applies X-rays to an examinee 210 who is laid on the bed 240. A high voltage generated by the high voltage generating unit 217 according to a control signal transmitted from the X-ray control unit is applied to the X-ray tube 211, and thus X-rays are applied from the X-ray tube 211 to the examinee 210.

The collimator 213 is a device that restricts the application range of X-rays applied from the X-ray tube 211. The application range of X-rays is set according to a control signal transmitted from the collimator control unit 221.

The detector 212 is a device that detects X-rays having penetrated the examinee 210 and measures the spatial distribution of the measures X-rays that have penetrated. The detector 212 is disposed opposite to the X-ray tube 211, and a large number of detection elements are two-dimensionally arrayed on the inside of a plane opposite to the X-ray tube 211. After signals measured by the detector are amplified by the preamplifier 222, the signals are converted into digital signals by the A/D converter 223. In the course of detection of X-rays by the detector 212 to conversion of digital signals by the A/D converter 223, system noise that is noise generated in a detector circuit is added to the digital signals. After that, various correction processes including logarithmic transformation processing are performed on the digital signals, and projection data is acquired.

The drive unit 214 rotates the X-ray tube 211 and the detector 212 around the examinee 210 according to a control signal transmitted from the scanner control unit 218. The application and detection of X-rays are performed together with the rotation of the X-ray tube 211 and the detector 212, and projection data is acquired at a plurality of projection angles. The unit of collecting projection angles is referred to as a view. In regard to the alignment of the two-dimensionally arrayed detection elements of the detector 212, the rotation direction of the detector 212 is referred to as a channel, and the direction orthogonal to the channel is referred to as a column. The projection data is identified from a view, a channel, and a column.

The bed control unit 219 controls the operation of the bed 240. The bed control unit 219 keeps the bed 240 standstill during the application and detection of X-rays, or moves the bed 240 in the Z-axis direction at a constant velocity. The scan while keeping the bed 240 standstill is referred to as an axial scan, and the scan while moving the bed 240 is referred to as a helical scan.

The central control unit 215 controls the operation of the scanner 200 described above according to instructions from the operation unit 250.

Next, the operation unit 250 will be described. The operation unit 250 has a reconstruction processing unit 251, an image processing unit 252, a storage unit 254, a display unit 256, an input unit 258, and the like.

The reconstruction processing unit 251 back-projects projection data acquired by the scanner 200, and reconstructs tomographic images. The image processing unit performs various image processes in order to reconstruct tomographic images to be images suited to diagnosis. The storage unit 254 stores projection data, tomographic images, and images after image processing. The display unit 256 displays tomographic image and images after image processing. The input unit 258 is used when the operator sets the acquiring conditions for projection data (tube voltages, tube currents, rotation speed, and the like) and the reconstruction conditions for tomographic images (a reconstruction filter, the size of a field of view (FOV), and the like).

Note that the operation unit 250 may be the medical image processing apparatus 1 shown in FIG. 1. In this case, the reconstruction processing unit 251 and the image processing unit 252 correspond to the CPU 2, the storage unit 254 corresponds to the storage device 4, the display unit 256 corresponds to the display device 7, and the input unit 258 corresponds to the input device 8.

Figure 3:
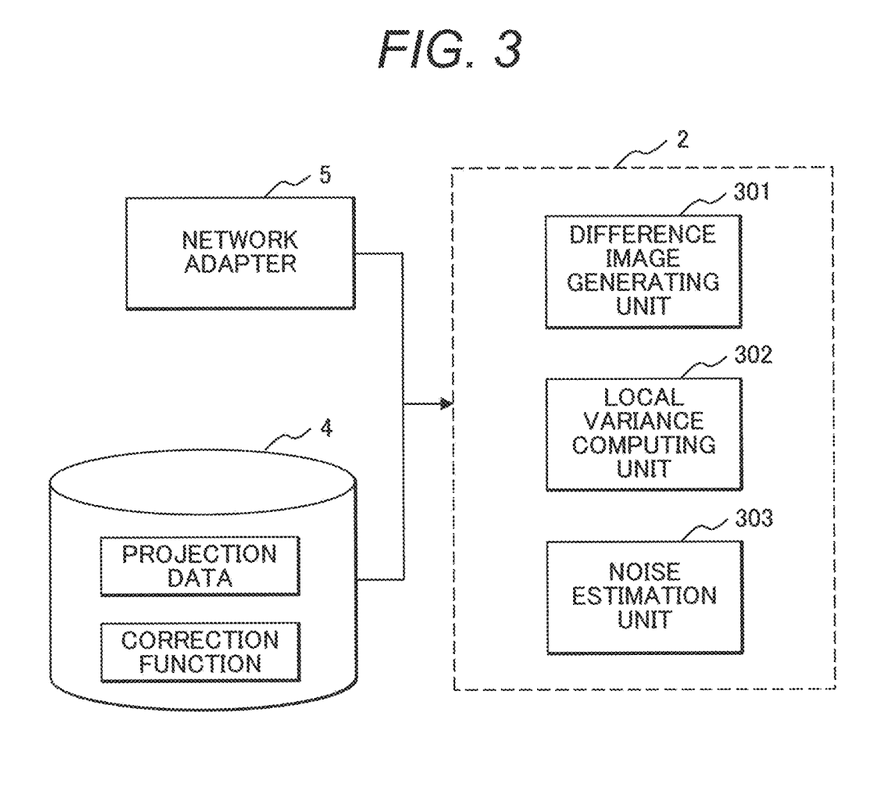
FIG. 3 is a functional block diagram of the medical image processing apparatus.

Referring to FIG. 3, a functional block diagram of the present embodiment will be described. Note that the functions shown in FIG. 3 may be configured of dedicated hardware using an Application Specific Integrated Circuit (ASIC), a Field-Programmable Gate Array (FPGA), and the like, or may be configured of software operating on the CPU 2. The following description, the present embodiment will be described in the case where the functions are configured of software.

The present embodiment includes a difference image generating unit 301, a local variance computing unit 302, and a noise estimation unit 303. The storage device 4 stores projection data acquired by the X-ray computed tomography apparatus 100 and correction functions and the like to be computed by process flows in FIG. 4. In the following, the component units will be described.

The a difference image between reconstructed tomographic images for every divided piece of projection data. For example, the pieces of projection data, which are divided into even-numbered views and odd-numbered views, are reconstructed to form two tomographic images, an even image and an odd image, and a difference image is created between the even image and the odd image. Since structures in the images are canceled from each other in the difference image between the even image and the odd image, the difference image to be created is an image having noise as a principal component.

Note that the projection data may be divided in any manner non-limiting to even-numbered views and odd-numbered views, as long as no artifact that is likely to interfere with diagnosis is generated in the tomographic image created from the divided projection data. Whether or not an artifact is generated is confirmed in advance using projection data acquired with the use of a uniform phantom.

The local variance computing unit 302 computes the local variance of the inputted image. The computed local variance corresponds to the noise intensity of the inputted image. For computation of the local variance, the following expression is used, for example.

$$\mathrm{Var}(i, j, k) = \frac{\sum_{\ell=-Ni/2}^{Ni/2} \sum_{m=-Nj/2}^{Nj/2} \sum_{n=-Nk/2}^{Nk/2} (p(\ell, m, n) - Ave(i, j, k))^2}{(Ni+1)(Nj+1)(Nk+1)}$$ [Mathematical Expression 1]

Here, i, j, and k are the coordinates of the pixels of a three-dimensional image, where i=1, 2, . . . , I, j=1, 2, . . . , J, k=1, 2, . . . , K. Note that i and j are the coordinates of the pixels of a tomographic image. Var(i,j,k) is local variance in proximity to Ni, Nj, Nk of the coordinates (i, j, k), and p(i, j, k) is the pixel value of the coordinates (i, j, k). Ave(i, j, k) is the mean of the pixel value in proximity to Ni, Nj, Nk of the coordinates (i, j, k), which is computed using the following expression, for example.

$$Ave(i, j, k) = \frac{\sum_{\ell=-Ni/2}^{Ni/2} \sum_{m=-Nj/2}^{Nj/2} \sum_{n=-Nk/2}^{Nk/2} p(\ell, m, n)}{(Ni+1)(Nj+1)(Nk+1)}$$ [Mathematical Expression 2]

When the difference image created at the difference image generating unit 301 is inputted to the local variance computing unit 302, the local variance of the difference image is computed.

The noise estimation unit 303 corrects the local variance of the difference image to be created at the difference image generating unit 301 using a correction function to be found in advance, and estimates noise intensity. The correction function according to the first embodiment includes system noise. The correction function is found using projection data acquired from a phantom having a known material or shape, and is stored in advance in a external device or the storage device 4 connected through the network adapter 5.

Here, prior to computing the correction function including system noise, the relationship between the local variance of the difference image to be created at the difference image generating unit 301 and noise intensity estimated by the noise estimation unit 303 is found. Since statistical fluctuations in the X-ray photon number follow the Poisson distribution, when the parameter of the Poisson distribution is set as an X-ray photon number z and the conversion gain at the A/D converter 223 is set as a, a variance VarX1 of a digital signal to be outputted from the A/D converter 223 is expressed by the following expression.

$$\mathrm{VarX1} = a \cdot \lambda$$ [Mathematical Expression 3]

Since logarithmic transformation processing is included in the course of conversion from the digital signal to projection data, a variance VarA of the projection data is expressed by the following expression.

$$\mathrm{VarA} = a/\lambda$$ [Mathematical Expression 4]

Note that it is assumed that in the course of derivation from Mathematical Expression 3 to Mathematical Expression 4, when a logarithmic transformation function is approximated by Taylor expansion to the quadratic term around 2, the coefficient of the term of VarX1^2 is small enough and thus can be ignored.

Subsequently, in the case where system noise c additively occurs in the variance of the digital signal, when the conversion gain in the A/D converter 223 is set as b, a variance VarX2 of the digital signal to be outputted from the A/D converter 223 is expressed by the following expression.

$$\mathrm{VarX2} = b \cdot \lambda + c$$ [Mathematical Expression 5]

Similarly to the course of derivation from Mathematical Expression 3 to Mathematical Expression 4, a variance VarD of projection data derived from Mathematical Expression 5 is expressed by the following expression.

$$VarD = \frac{b \cdot \lambda + c}{\lambda^2}$$ [Mathematical Expression 6]

Although Mathematical Expression 6 has two solutions in regard to λ, the solution that is negative under the condition VarD>0 and c>0 is inappropriate as the X-ray photon number, and thus λ is the following expression.

$$\lambda = \frac{b + \sqrt{b^2 + 4VarD \cdot c}}{2VarD}$$ [Mathematical Expression 7]

It is assumed that the difference image between the tomographic images reconstructed for every divided piece of projection data is created from projection data having of Mathematical Expression 6 and the tomographic image reconstructed with projection data before divided is created from having the variance VarA of Mathematical Expression 4. In the case where these pieces of projection data are acquired by detecting the same X-rays, the X-ray photon number N of Mathematical Expression 4 matches the X-ray photon number z Mathematical Expression 6, and thus the following expression is obtained.

$$VarA = \frac{VarD}{\alpha + \sqrt{\alpha^2 + \beta \cdot VarD}}$$ [Mathematical Expression 8]

where $$\alpha = \frac{b}{2a}, \beta = \frac{c}{a^2}$$

α and β in Mathematical Expression 8 are formed in functions of distance s from the rotation center of the scanner 200, and Mathematical Expression 8 is expressed as the following expression.

$$VarA = \frac{VarD}{\alpha(s) + \sqrt{\alpha(s)^2 + \beta(s) \cdot VarD}}$$ [Mathematical Expression 9]

Mathematical Expression 9 is an expression that expresses the relationship between the variance VarD and the variance VarA, and also expresses the relationship between the local variance of the difference image to be created at the difference image generating unit 301 and the local variance of the tomographic image reconstructed with projection data before divided, which corresponds to noise intensity estimated by the noise estimation unit 303. α(s) and β(s) are correction functions that correct the variance VarD to the variance VarA, and are found in advance for estimating the noise intensity of the tomographic image of the examinee.

Figure 4:
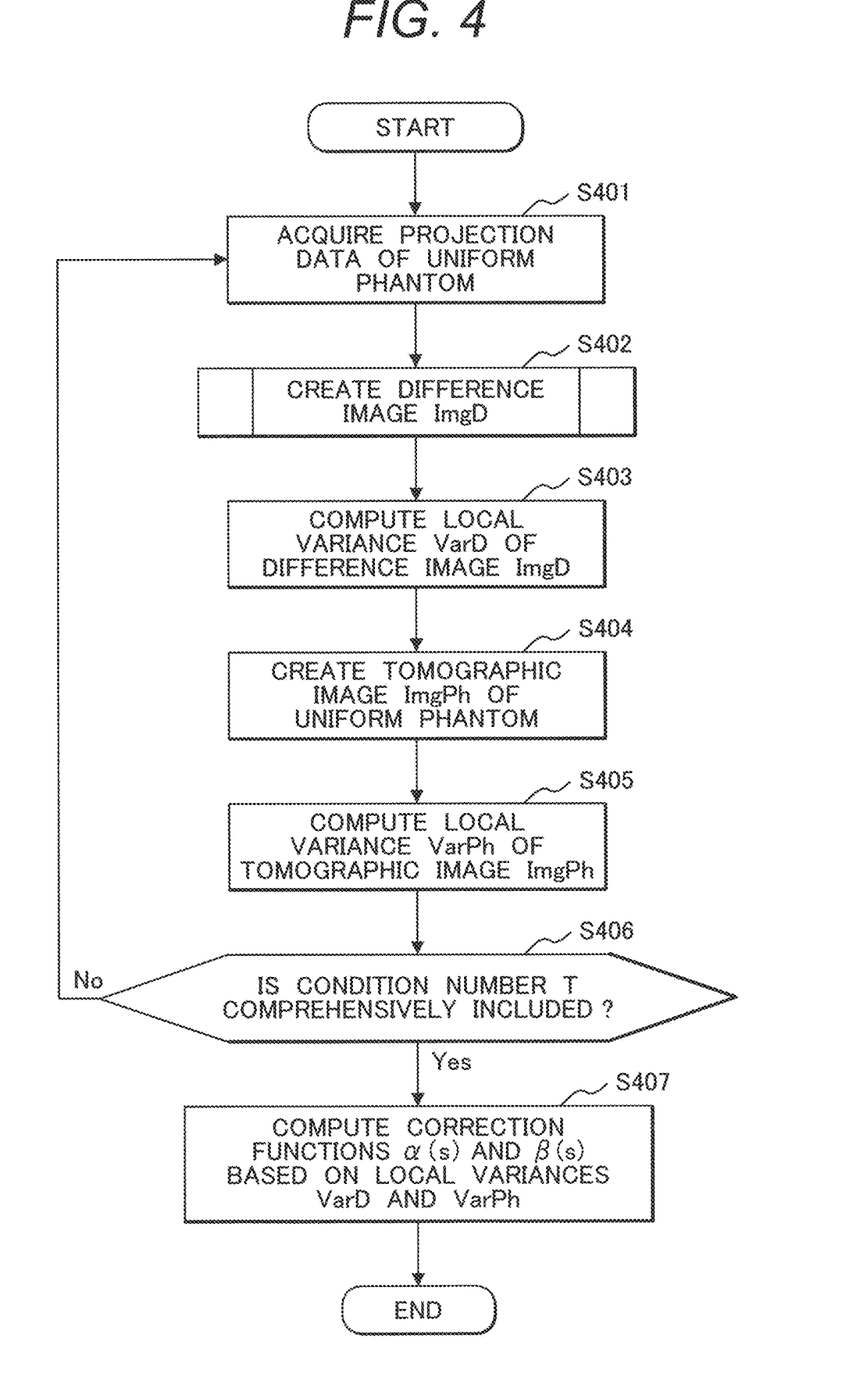
FIG. 4 is a diagram showing an example of a flow of a computation process of a correction function.

Referring to FIG. 4, an example of a flow of processes for computing the correction functions will be described step by step.

(Step S401)

The difference image generating unit 301 acquires projection data in a cylinder-shaped phantom filled with a uniform substance. The projection data of the phantom is acquired in the state where the center of the phantom is placed in the rotation center of the scanner 200. The diameter of the phantom is desirably nearly equal to its imaging visual field.

(Step S402)

Figure 5:
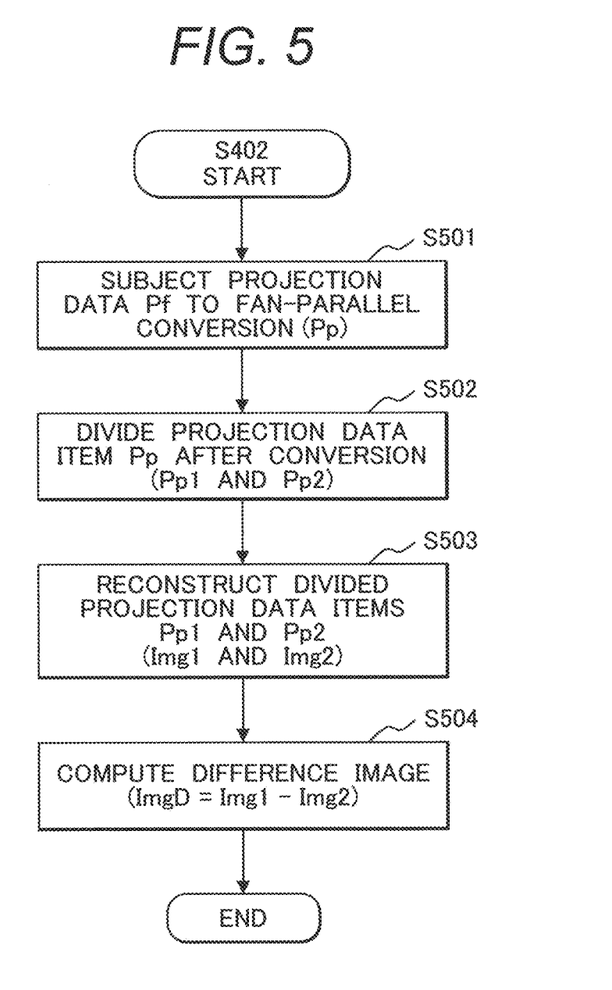
FIG. 5 is a diagram showing an example of a flow of a creation process of a difference image.

The difference image generating unit 301 divides the projection data of the phantom, and creates a difference image ImgD between the tomographic images reconstructed for every divided piece of projection data. Referring to FIG. 5, an example of a flow of processes in the present step will be described.

(Step S501)

The difference image generating unit 301 converts a projection data item Pf in a fan beam form into a projection data item Pp in a parallel beam form. As exemplified in FIG. 6A, the projection data in a fan beam is in a data format based on a geometric system when an X-ray beam 601, which is applied from the X-ray tube 211 in a fan-shaped spread to penetrate the examinee 210, enters the detector 212 in a curved surface shape. On the other hand, as exemplified in FIG. 6B, the projection data in a parallel beam form is in a data format based on a geometric system when an X-ray beam 601, which is applied from a plurality of X-ray tubes 211 in parallel with each other to penetrate the examinee 210, enters the detector 212 in a flat surface shape.

Figure 6A:
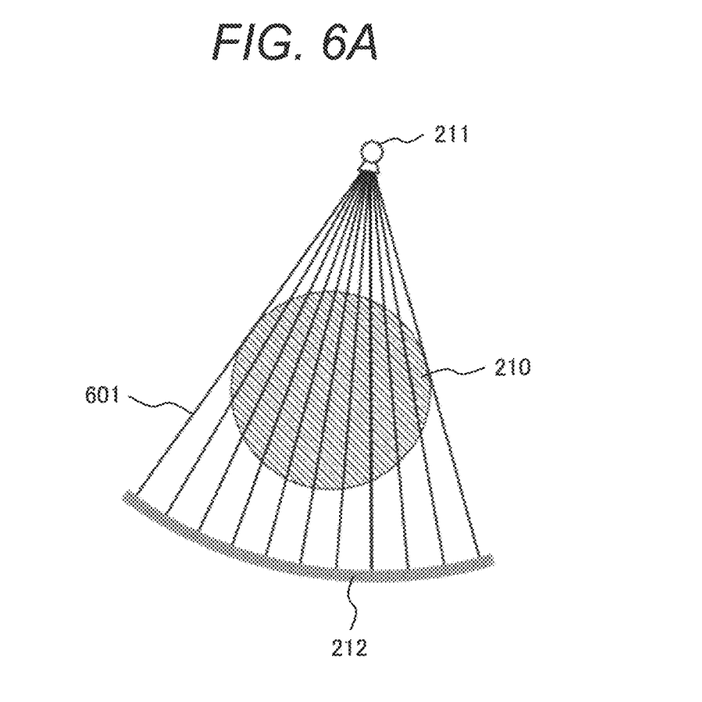
FIG. 6A is a diagram describing the projection data of a fan beam form.
Figure 6B:
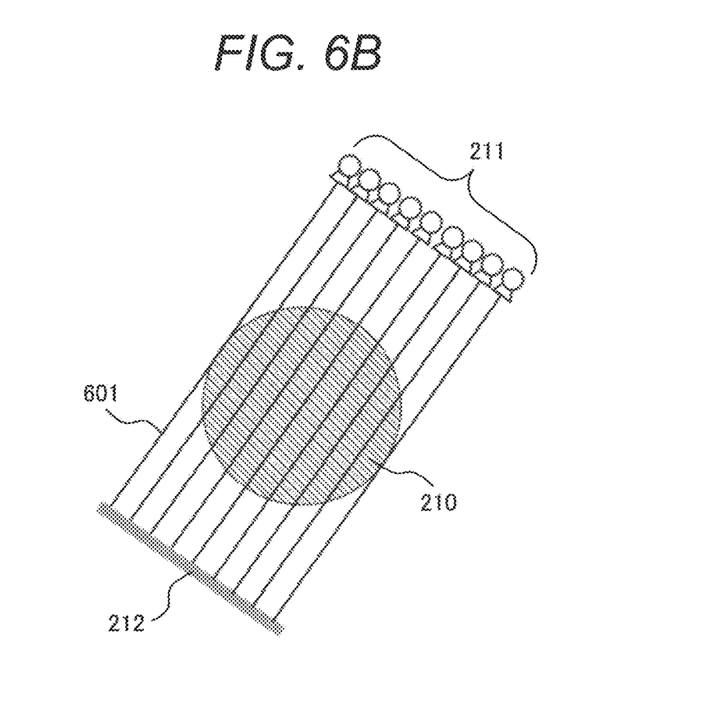
FIG. 6B is a diagram describing the projection data of a parallel beam form.

In the first embodiment, the projection data item Pf in a fan beam form, which can be acquired by even one X-ray tube 211, is converted into the projection data item Pp in a parallel beam form by fan-parallel conversion. The spatial resolution of the tomographic image reconstructed from the projection data item Pp in a parallel beam form is made more uniform.

(Step S502)

The difference image generating unit 301 divides the projection data item Pp converted in Step S501 into two projection data items Pp1 and Pp2. For example, the projection data item Pp1 is projection data of an odd-numbered view, and the projection data item Pp2 is projection data of an even-numbered view.

(Step S503)

The difference image generating unit 301 reconstructs the projection data items Pp1 and Pp2 divided in Step S502, and creates two tomographic images Img1 and Img2. Note that the tomographic image Img1 is created by reconstructing the projection data item Pp1 and the tomographic image Img2 is created by reconstructing the projection data item Pp2.

(Step S504)

The difference image generating unit 301 computes the difference image ImgD using the two tomographic images Img1 and Img2 created in Step S503. The difference image ImgD is computed as Img1-Img2, for example, by differencing the pixels of the other tomographic image from the pixels of one tomographic image.

The description returns to FIG. 4.

(Step S403)

The local variance computing unit 302 computes the local variance VarD of the difference image ImgD created in Step S402. For computing the local variance VarD, Mathematical Expression 1, for example, is used.

(Step S404)

The projection data of the phantom acquired in Step S401 is reconstructed, and a tomographic image ImgPh of the phantom is created. Note that Img1+Img2, which is an image of the two tomographic images Img1 and Img2 created in Step S503, may be created as the tomographic image ImgPh.

(Step S405)

The local variance computing unit 302 computes a local variance VarPh of the tomographic image ImgPh of the phantom created in Step S404. For computing the local variance VarPh, Mathematical Expression 1, for example, is used.

(Step S406)

It is determined whether or not a condition number T relating to the X-ray photon number is comprehensively included. When the condition number T is comprehensively included, the process goes to Step S407, and when the condition number T is not comprehensively included, the condition relating to the X-ray photon number, the value of the tube current, for example, is changed, and then the process returns to Step S401. The processes from Steps S401 to S405 are repeated, a local variance VarD(t) is computed in Step S403, and a local variance VarPh(t) is computed in Step S405 for each condition relating to the X-ray photon number. Note that t is the index of the condition relating to the X-ray photon number, t=1, 2, . . . , T. (Step S407)

The correction functions α(s) and β(s) are computed based on the local variance VarD(t) computed in Step S403 and the local variance VarPh(t) computed in Step S405. In the case where the center of the tomographic image matches the rotation center of the scanner 200, the distance s from the pixel at the coordinates (i,j) to the rotation center is expressed by the following expression.

$$s=\sqrt{\{i-(I+1)/2\}^2+\{j-(J+1)/2\}^2}$$ [Mathematical Expression 10]

The following expressions are used as the correction functions α(s) and β(s) are n-dimensional polynomial equations of the distance s.

$$\alpha(s) = r_n \cdot s^n + r_{n-1} \cdot s^{n-1} + \cdots + r_0 \quad \text{[Mathematical Expression 11]}$$

$$\beta(s) = q_n \cdot s^n + q_{n-1} \cdot s^{n-1} + \cdots + q_0 \quad \text{[Mathematical Expression 12]}$$

A set of rn, . . . , r0 of the coefficient Mathematical Expression 11 and a set of qn, . . . , q0 of the coefficient of Mathematical Expression 12 are determined as a combination that gives the minimum value of the following expression.

$$\Psi(r_0, \cdots, r_n, q_0, \cdots, q_n) = \quad \text{[Mathematical Expression 13]}$$

$$\sum_{t=1}^{T} \left\{ VarPh(t) - \frac{VarD(t)}{\alpha(s) + \sqrt{\alpha(s)^2 + \beta(s) \cdot VarD(t)}} \right\}^2$$

By determining a set of rn, . . . , r0, qn, . . . , q0 of the coefficient, the correction functions α(s) and β(s) are computed.

The computed correction functions α(s) and β(s) are stored in the storage device 4 or in an external device connected through the network adapter 5. Note that the correction functions α(s) and β(s) are desirably computed for each of the imaging conditions, such as for each of voltages to be applied to the X-ray tube 211 or for each of types of X-ray filters.

From the flows of the processes described above, the correction functions α(s) and β(s) are computed based on the projection data of the uniform phantom. The computed correction functions α(s) and β(s) are used for estimating the noise intensity of the tomographic image of the examinee.

Figure 7:
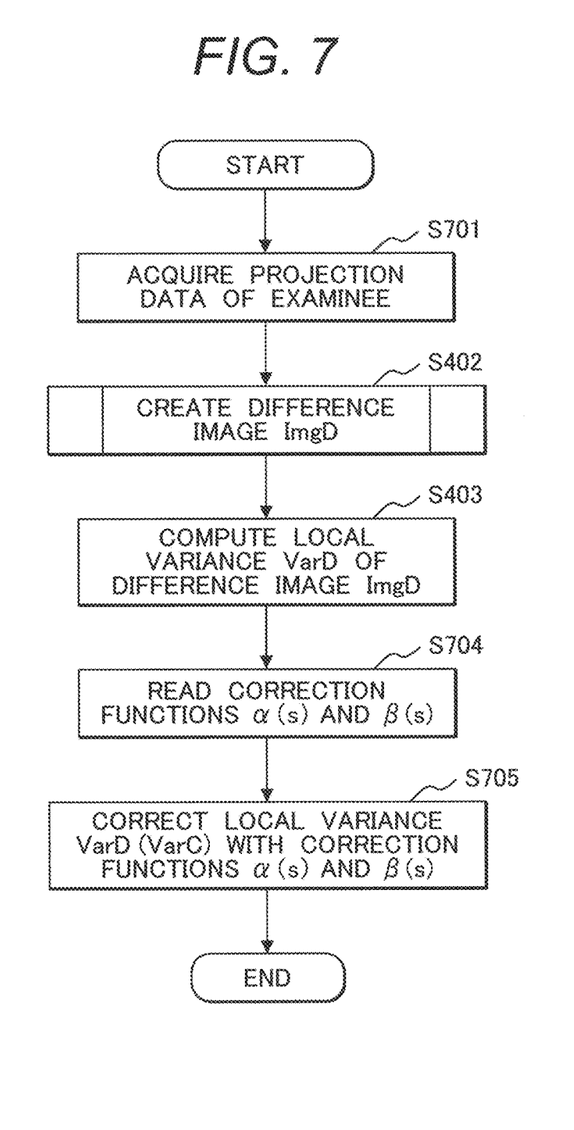
FIG. 7 is a diagram showing an example of a flow of a noise estimation process for the tomographic image of an examinee.

Referring to FIG. 7, an example of a flow of processes of estimating the noise intensity of the tomographic image of the examinee will be described step by step. Note that the description of the steps overlapping with FIG. 4 will be simplified.
(Step S701)
The projection data of the examinee is acquired. The projection data of the examinee is read from the storage device 4 or an external device connected through the network adapter 5.
(Step S402)
The difference image generating unit 301 divides the projection data of the examinee, and creates the difference image ImgD between the tomographic images reconstructed for every divided piece of projection data.
(Step S403)
The local variance computing unit 302 computes the local variance VarD of the difference image ImgD created in Step S402. For computing the local variance VarD, Mathematical Expression 1, for example, is used.
(Step S704)
The noise estimation unit 303 reads the correction functions α(s) and β(s) from the storage device 4 or an external device connected through the network adapter 5. The correction functions α(s) and β(s) to be read are desirably selected based on the imaging conditions when the projection data of the examinee is acquired.
(Step S705)
The noise estimation unit 303 corrects the local variance VarD computed in Step S403 with the correction functions α(s) and β(s) read in Step S704, and computes a local variance VarC after corrected. For computing the local variance VarC after corrected, the following expression, for example, is used.

$$VarC = \frac{VarD}{\alpha(s) + \sqrt{\alpha(s)^2 + \beta(s) \cdot VarD}} \quad \text{[Mathematical Expression 14]}$$

The computed local variance VarC is outputted as the estimation value of the noise intensity of the tomographic image of the examinee. That is, the noise estimation unit estimates the noise intensity of the tomographic image of the examinee as the local variance VarC. A noise intensity map may be created by mapping the noise intensity estimated as the local variance VarC at the coordinates (i,j) of the tomographic image.

Using the correction functions α(s) and β(s) found in advance from the flows of the processes described above, the noise intensity of the tomographic image of the examinee is estimated. Since the correction functions α(s) and β(s) includes the system noise c, it is possible to maintain the estimation accuracy of noise intensity even though the ratio of the system noise c rises. The correction functions α(s) and β(s) are found for each of the imaging conditions, and thus the correction of the local variance suited to the imaging conditions is made possible. Accordingly, it is possible to improve the estimation accuracy of noise intensity.

Note that the division of the projection data is not limited to the view direction. As long as the structures are cancelled in the difference image, the projection data may be divided in the channel direction or in the lateral direction, or may be divided in three directions mixed. The split number of the projection data is not limited to two, which may be three or more.

Second Embodiment

In the first embodiment, the estimation of noise intensity in the entire tomographic image of the examinee is described. In the second embodiment, a reduction in noise based on the noise intensity of the Region Of Interest (ROI) set in a tomographic image will be described. Note that difference from the first embodiment is that some steps are added in the processes in FIG. 7, and the description of the points other than these is omitted.

Figure 8:
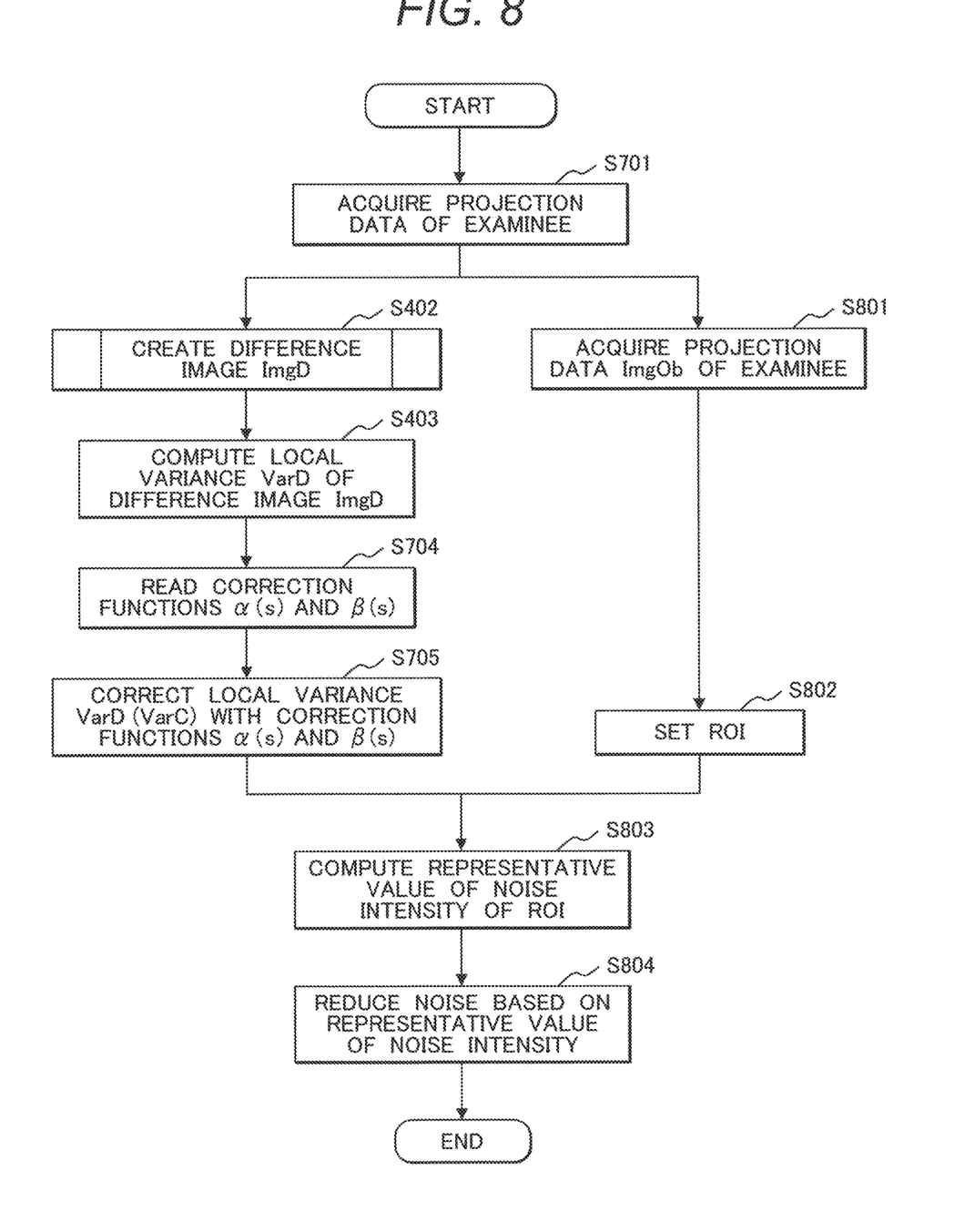
FIG. 8 is a diagram showing an example of a flow of a noise reduction process.
Figure 9:
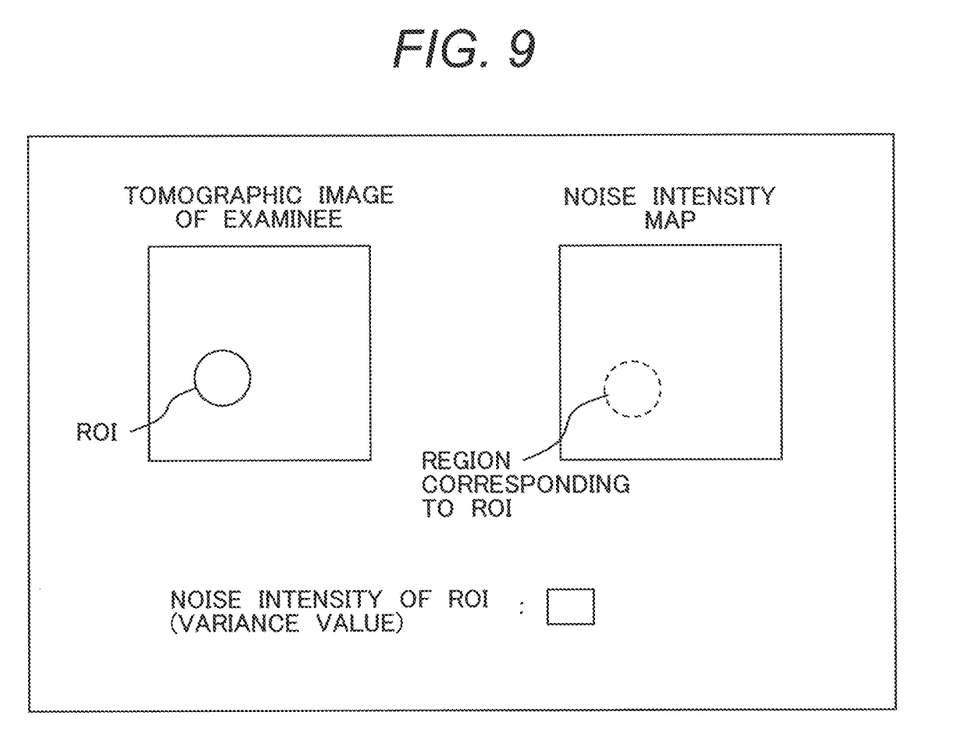
FIG. 9 is a diagram showing an example of an ROI setting screen.

Referring to FIG. 8, an example of a flow of processes in the second embodiment will be described step by step. Note that the description of the steps overlapping with FIG. 7 will be simplified.
(Step S701)
The projection data of an examinee is acquired.
(Step S402)
A difference image generating unit 301 divides the projection data of the examinee, and creates a difference image ImgD between tomographic images reconstructed for every divided piece of projection data.
(Step S403)
A local variance computing unit 302 computes a local variance VarD of the difference image ImgD created in Step S402.
(Step S704)
A noise estimation unit 303 reads the correction functions α(s) and R(s).
(Step S705)
The noise estimation unit 303 computes a local variance VarC after correction.
(Step S801)
By reconstructing the projection data of the examinee acquired in Step S701, a tomographic image ImgOb of the examinee is created.
(Step S802)
To a tomographic image ImgOb, an operator sets an ROI. For setting the ROI, a screen exemplified in FIG. 9 is used, for example. On the screen in FIG. 9, a noise intensity map on which the local variance VarC computed in Step S705 is mapped is displayed together with the tomographic image ImgOb of the examinee. The operator sets the ROI in a region in which noise is desired to reduce, for example, through the input device 8 while making reference to the noise intensity map. The shape of the ROI is arbitrary, and the shape may be a circular shape or a rectangle, for example. Mathematical Expression of the ROI to be set is also arbitrary.
(Step S803)
The representative value of the noise intensity of the ROI set in Step S802 is computed. For example, the mean value or the maximum value of the local variance in the ROI is computed as the representative value.
(Step S804)
A noise reduction process is applied to the tomographic image ImgOb based on the representative value of the noise intensity computed in Step S803. The noise reduction process may be a given process. For example, a parameter q expressing the degree of smoothing may be computed as $\eta = t \cdot \delta^v$ using a representative value δ of the noise intensity, and a smoothing process may be applied to the tomographic image ImgOb according to the computed η. Note that t and v are given constants.

From the flows of the processes described above, since the noise reduction process is applied to the tomographic image based on the noise intensity of the ROI set by the operator, the tomographic image with the improved Signal-Noise Ratio (SNR) of the ROI is obtained.

Note that the medical image processing apparatus and the medical image processing method according to the present invention are not limited to the foregoing embodiments, and can be embodied with the components modified within the scope not deviating from the gist of the present invention. Furthermore, a plurality of components disclosed in the foregoing embodiments may be appropriately combined. moreover, some components may be removed from all the components described in the foregoing embodiments.

REFERENCE SIGNS LIST

1: medical image processing apparatus,
2: CPU,
3: memory,
4: storage device,
5: network adapter,
6: system bus,
7: display device,
8: input device,
10: medical imaging apparatus,
11: medical image database,
100: X-ray computed tomography apparatus,
200: scanner,
210: examinee,
211: X-ray tube,
212: detector,
213: collimator,
214: drive unit,
215: central control unit,
216: X-ray control unit,
217: high voltage generating unit,
218: scanner control unit,
219: bed control unit,
221: collimator control unit,
222: preamplifier,
223: A/D converter,
240: bed,
250: operation unit,
251: reconstruction processing unit,
252: image processing unit,
254: storage unit,
256: display unit,
258: input unit,
301: difference image generating unit,
302: local variance computing unit,
303: noise estimation unit,
601: X-ray beam

What is claimed is:

1. A medical image processing apparatus comprising:
a difference image generating unit that divides projection data obtained by applying radiation to an examinee to create a difference image between tomographic images reconstructed for every divided piece of projection data;
a local variance computing unit that computes local variance in the difference image; and
a noise estimation unit that corrects the local variance using a correction function, the correction function having been found in advance, to estimate noise intensity of a tomographic image of the examinee,
wherein the correction function includes system noise.

2. The medical image processing apparatus according to claim 1, wherein when the local variance is VarD, the noise intensity is VarC, a distance from a rotation center of a scanner is s, and the correction function is α(s) and β(s), the noise intensity VarC is computed from $$VarC = \frac{VarD}{\alpha(s) + \sqrt{\alpha(s)^2 + \beta(s) \cdot VarD}}.$$

3. The medical image processing apparatus according to claim 2, wherein the correction functions α(s) and β(s) are found for each of imaging conditions based on projection data of a phantom filled with a uniform substance.

4. The medical image processing apparatus according to claim 1, wherein the noise estimation unit creates a noise intensity map by mapping the noise intensity, and displays the noise intensity map together with a tomographic image of the examinee.

5. The medical image processing apparatus according to claim 4, wherein a noise reduction process is applied to the tomographic image of the examinee based on noise intensity of a ROI set in the tomographic image of the examinee.

6. The medical image processing apparatus according to claim 1, wherein the system noise is noise generated in a detector circuit in a course of detection of the radiation to conversion of a digital signal.

7. A medical image processing apparatus comprising:
a difference image generating unit that divides projection data obtained by applying radiation to an examinee to create a difference image between tomographic images reconstructed for every divided piece of projection data;
a local variance computing unit that computes local variance in the difference image; and
a noise estimation unit that corrects the local variance using a correction function found in advance to estimate noise intensity of a tomographic image of the examinee,
wherein the correction function includes system noise, and
wherein the system noise is noise generated in a detector circuit in a course of detection of the radiation to conversion of a digital signal.

8. The medical image processing apparatus according to claim 7, wherein when the local variance is VarD, the noise intensity is VarC, a distance from a rotation center of a scanner is s, and the correction function is α(s) and β(s), the noise intensity VarC is computed from $$\text{Var}C = \frac{\text{Var}D}{\alpha(s) + \sqrt{\alpha(s)^2 + \beta(s) \cdot \text{Var}D}}.$$

9. The medical image processing apparatus according to claim 8, wherein the correction functions α(s) and β(s) are found for each of imaging conditions based on projection data of a phantom filled with a uniform substance.

10. The medical image processing apparatus according to claim 7, wherein the noise estimation unit creates a noise intensity map by mapping the noise intensity, and displays the noise intensity map together with a tomographic image of the examinee.

11. The medical image processing apparatus according to claim 10, wherein a noise reduction process is applied to the tomographic image of the examinee based on noise intensity of a ROI set in the tomographic image of the examinee.

12. A medical image processing method comprising:
a difference image creating step in which projection data obtained by applying radiation to an examinee is divided to create a difference image between tomographic images reconstructed for every divided piece of projection data;
a local variance computing step wherein local variance is computed in the difference image; and
a noise estimating step wherein the local variance is corrected using a correction function, the correction function having been found in advance, to estimate noise intensity of a tomographic image of the examinee,
wherein the correction function includes system noise.

13. The medical image processing method according to claim 12, wherein the system noise is noise generated in a detector circuit in a course of detection of the radiation to conversion of a digital signal.

14. The medical image processing method according to claim 12, wherein when the local variance is VarD, the noise intensity is VarC, a distance from a rotation center of a scanner is s, and the correction function is α(s) and β(s), the noise intensity VarC is computed from $$\text{Var}C = \frac{\text{Var}D}{\alpha(s) + \sqrt{\alpha(s)^2 + \beta(s) \cdot \text{Var}D}}.$$

15. The medical image processing method according to claim 14, wherein the correction functions α(s) and β(s) are found for each of imaging conditions based on projection data of a phantom filled with a uniform substance.

16. The medical image processing method according to claim 12, further comprising:
creating a noise intensity map by mapping the noise intensity; and
displaying the noise intensity map together with a tomographic image of the examinee.

17. The medical image processing method according to claim 16, further comprising:
applying a noise reduction process to the tomographic image of the examinee based on noise intensity of a ROI set in the tomographic image of the examinee.

* * * * *